United States Patent [19]

Anderson et al.

[11] 4,169,036
[45] Sep. 25, 1979

[54] SYSTEM FOR LOADING SLAB-GEL HOLDERS FOR ELECTROPHORESIS SEPARATION

[75] Inventors: Norman G. Anderson, Hinsdale; Norman L. Anderson, Willowbrook, both of Ill.

[73] Assignee: The United States of America as represented by the United States Department of Energy, Washington, D.C.

[21] Appl. No.: 889,691

[22] Filed: Mar. 24, 1978

[51] Int. Cl.$^2$ .................... G01N 27/28; G01N 33/16
[52] U.S. Cl. ........................... 204/299 R; 204/180 G
[58] Field of Search ............. 204/180 G, 299; 424/12; 23/230 B

[56] References Cited

U.S. PATENT DOCUMENTS

| | | | |
|---|---|---|---|
| 3,856,655 | 12/1974 | Roberts | 204/299 R |
| 3,932,265 | 1/1976 | Hoefer | 204/299 R |
| 3,989,612 | 11/1976 | Kragt et al. | 204/299 R |
| 4,035,377 | 7/1977 | Detroy | 204/299 R |
| 4,049,534 | 9/1977 | Posner | 204/299 R |

OTHER PUBLICATIONS

Reid et al., "A Simple Apparatus for Vertical Flat-Sheet Polyacrylamide Gel Electrophoresis," *Anal. Biochem.*, vol. 22, pp. 374–381, (1968).
O'Farrell, "High Resolution Two-Dimensional Electrophoresis of Proteins," *Jrnl. of Biol. Chem.*, vol. 250, No. 10, pp. 4007–4021, (1975).

*Primary Examiner*—Arthur C. Prescott
*Attorney, Agent, or Firm*—Dean E. Carlson; Frank H. Jackson; Hugh W. Glenn

[57] ABSTRACT

A slab-gel loading system includes a prismatic chamber for filling a plurality of slab-gel holders simultaneously. Each slab-gel holder comprises a pair of spaced apart plates defining an intermediate volume for gel containment. The holders are vertically positioned in the chamber with their major surfaces parallel to the chamber end walls. A liquid inlet is provided at the corner between the bottom and a side wall of the chamber for distributing a polymerizable monomer solution or a coagulable colloidal solution into each of the holders. The chamber is rotatably supported so that filling can begin with the corner having the liquid inlet directed downwardly such that the solution is gently funneled upwardly, without mixing, along the diverging side and bottom surfaces. As filling proceeds, the chamber is gradually rotated to position the bottom wall in a horizontal mode. The liquid filling means includes a plastic envelope with a septum dividing it into two compartments for intermixing two solutions of different density and thereby providing a liquid flow having a density gradient. The resulting gels have a density gradient between opposite edges for subsequent use in electrophoresis separations.

7 Claims, 2 Drawing Figures

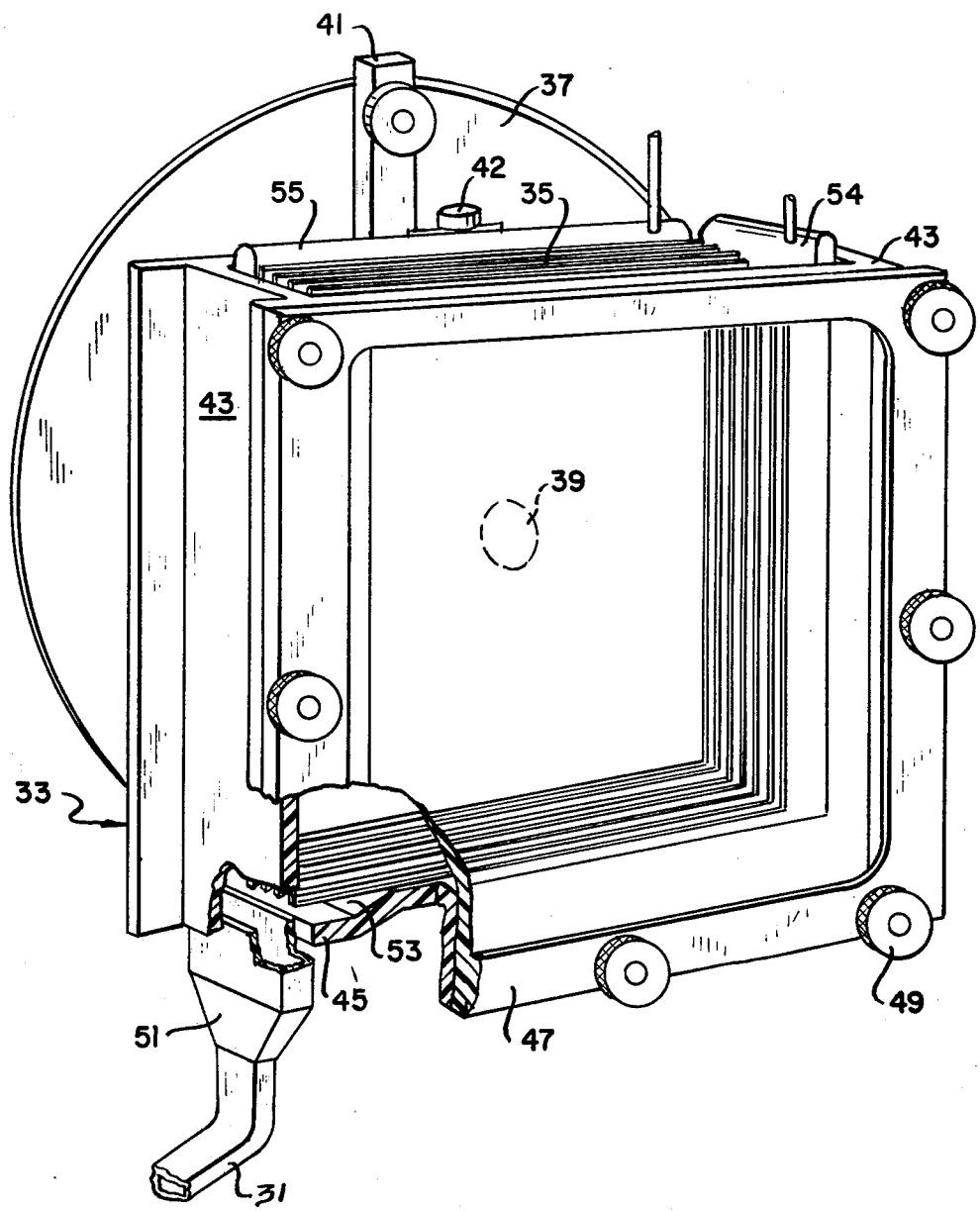

SYSTEM FOR LOADING SLAB-GEL HOLDERS FOR ELECTROPHORESIS SEPARATION

CONTRACTUAL ORIGIN OF THE INVENTION

The invention described herein was made in the course of, or under, a contract with the U.S. DEPARTMENT OF ENERGY.

BACKGROUND OF THE INVENTION

The present invention relates to a system for filling slab-gel holders with coagulable solution which subsequently solidifies into the gel form. For purposes of this application, the term "coagulable solution" is intended to comprehend both monomer solutions and colloidal sols that are capable of polymerizing or coagulating to form gels. Also the term "coagulate" is intended to include the processes of monomer polymerization and that of sol coagulation to produce gels. The gels are often provided with a density gradient across the slab. These gradient gels are prepared by filling the holder with a coagulable solution flow of continually changing density. The liquid fill for the gradient gels is therefore termed a gradient solution or merely a gradient.

The gels are used for electrophoresis separation of material such as protein; protein subunits and nucleic acids. Such separations are often the second separation in a two-dimensional separation system. The procedure begins with the isoelectric separation of species along a thin, elongated or spaghetti-like gel medium. In this original separation, the proteins, amino acids or other species migrate to a previously established pH point within the gel at which the sample is electrically neutral. These separations are quite well known and can be followed by a second dimensional electrophoresis separation to provide a high resolution of protein and protein subunits. In the electrophoresis separation, sample species migrate through a gel acting as a sieve to a point determined by their molecular weight.

The initial isoelectric separation and the second electrophoresis separation are both more fully described in the assignee's U.S. Pat. 4,088,561 filed May 1978, by Norman L. Anderson, entitled "Apparatus for Electrophoresis Separation." This application is expressly incorporated herein by reference. The electrophoresis separation is performed across an acrylamide gel containing sodium dodecyl sulfate (SDS) employed to negate the isoelectric effect. Gel compositions are well known and include polymerization as well as cross linking agents along with a gel buffer. Gels of thess types have previously been assembled manually between glass plates with laboratory clamping devices and subjected to electric current between separate upper and lower buffer solutions. Previous filling operations ordinarily were performed one at a time and then transferred to the apparatus for conducting the electrophoresis separation. These procedures are quite cumbersome and time-consuming when a large number of samples must be run, as in genetic screening surveys and clinical diagnostic applications. The prior art devices for the filling of the slab-gel holders have generally provided for filling from the top which may promote intermixing of gradient portions of different density. Prior to coagulation, the solution, sealed in by agar, has tended to leak and make the process more difficult to accomplish.

PRIOR ART STATEMENt

The following publications describe previous systems slab-gel formation.

Reid and Bieleski, "A Simple Apparatus for Vertical Flat-Sheet Polyacrylamide Gel Electrophoresis", Analytical Biochemistry, 22, 374-381 (1968). This article describes the filling of a single slab-gel holder from a slot within the upper holder portion while manually tilting the apparatus so that air bubbles do not become trapped. The article does not suggest a system for simultaneously filling a plurality of holders from the bottom with a gradient while using the bottom and side surfaces for gently diverging the flow as it enters the holder. O'Farrell, "High Resolution, Two Dimensional Electrophoresis of Protein", *The Journal of Biological Chemistry*, Vol. 250, No. 10, 4007-4021, May 25, 1975. The procedure described in this publication allows for the filling of one holder at a time from an upper slot within the holder plates.

Neither of these articles describe or show the apparatus of the present application, as summarized below.

SUMMARY OF THE INVENTION

In view of the problems associated with the prior art systems, it is an object of the present invention to provide a slab-gel filling system that permits the simultaneous filling of a plurality of slab-gel holders.

It is a further object to provide a system for slab gel filling in which a coagulable solution exhibiting an increasing density gradient can be filled with minimal mixing of its portions having different density.

It is a further object to provide a system for liquid filling including an easily replaceable device for gradient formation.

In accordance with the present invention, a slab-gel preparation system includes a prismatic chamber for containing a plurality of slab-gel holders. The chamber has a bottom surface, parallel end surfaces and at least two side surfaces with the slab-gel holders arranged in an array with their major surfaces generally parallel to the end surfaces of the prismatic chamber. Each of the holders includes a pair of spaced apart plates defining an intermediate volume for containing the slab gel. The prismatic chamber is rotatably supported about an axis passing transversely through its end surfaces and the slab-gel holders. The chamber includes an inlet for a gradient solution flow at a lower longitudinal corner between the bottom and side surfaces. Also included in this system are means for preparing and feeding a gradient flow with increasing density into the chamber inlet. Provisions are made for rotatably positioning the prismatic chamber with the inlet corner pointed downwardly such that the bottom and side surfaces diverge upwardly from the gradient inlet at the beginning of the filling operation. The chamber is provided so that it can be continuously and gently rotated towards the horizontal during gradient filling to minimize mixing between portions of different density. When the chamber and slab-gel holders are filled, the bottom chamber wall is horizontal to allow the gradient solution to transform into a gel of decreasing density from the bottom to the upper surface.

More specific aspects of the invention include a flexible plastic envelope having first and second compartments separated by a curved septum. The septum is preferably a thermally fused bond between the two opposing envelope sides. Solutions of different density are filled in the two compartments and are permitted to flow together from respective outlets to form a solutiom flow of continuously increasing density. Also, a portion of the system permits displacing the coagulable solution immediately after filling the slab-gel holders with a liquid which will not solidify.

BRIEF DESCRIPTION OF THE DRAWINGS

The present invention is illustrated in the accompanying drawings wherein:

FIG. 2 is a perspective view of the prismatic chamber with slab-gel holders in place after filling is complete.

DETAILED DESCRIPTION OF THE INVENTION

Figure 1:
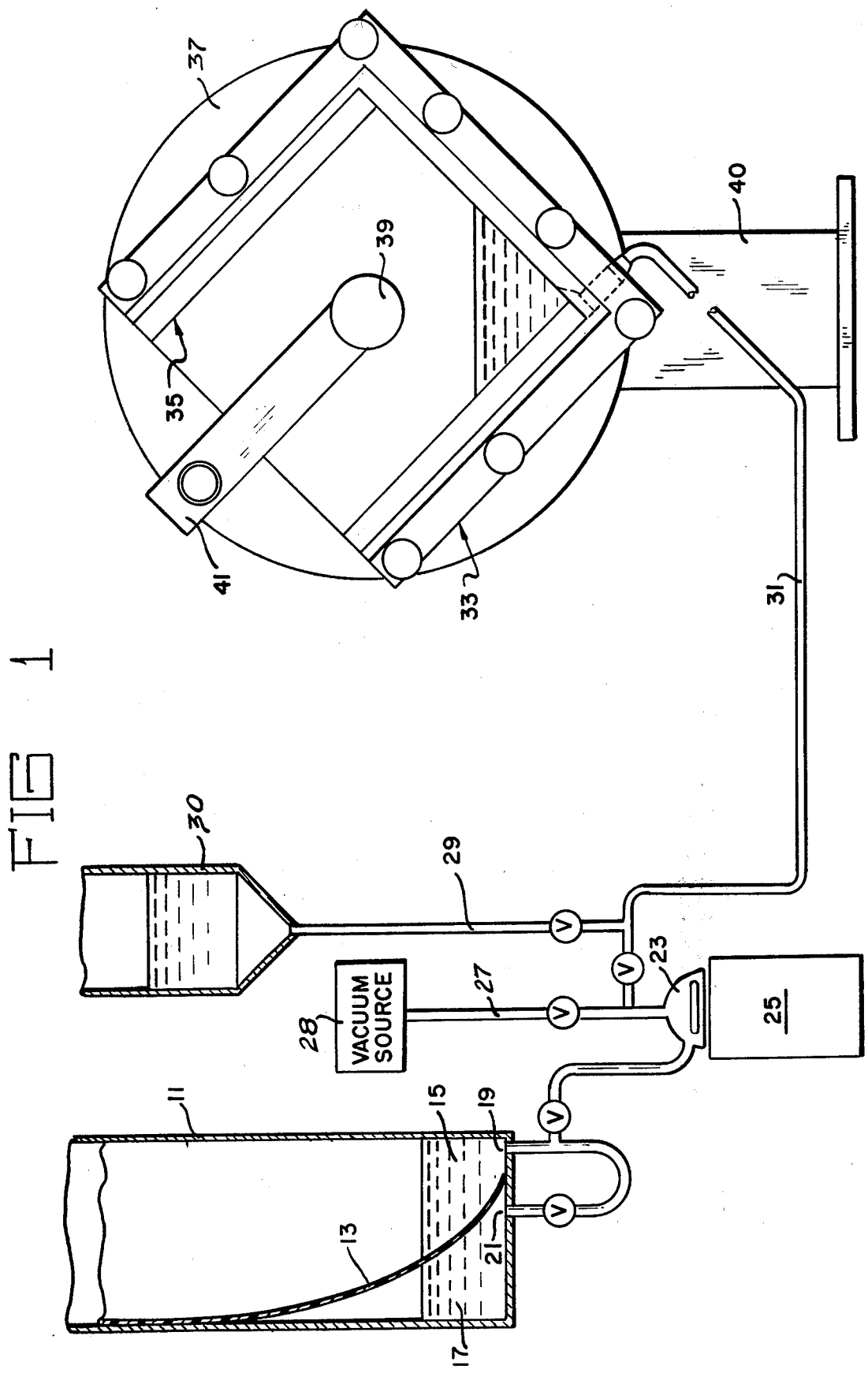
FIG. 1 is a schematic illustration of a slab-gel filling system.

A system for filling a plurality of slab gels is illustrated in FIG. 1. A container or envelope 11 containing coagulable solution is divided into two compartments 15, 17 by a septum 13 passing from top to bottom along the envelope. The two compartments 15, 17 include outlets 19, 21 which merge together for flow into a mixing vessel 23. A magnetic mixer 25 is illustrated for providing agitation within the mixing vessel 23. The discharge line from the mixing vessel is provided with a suitable valving arrangement and connections such as 27 connected to vacuum source 28 for providing a flush of the coagulable solution within envelope 11. Connection 29 permits the introduction of a dense noncoagulable liquid from container 30 to displace the solution within the downstream line 31. A dye can be added to the liquid in container 30 to monitor this displacement in a transparent system.

The mixing chamber 23 is connected by fluid line 31 to a rotatably mounted chamber 33 adapted to contain a plurality of slab-gel holders 35. Chamber 33 is axially mounted on a rotatable shaft 39 near to a stationary indexing wheel 37. A locking device 41 rotates on shaft 39 with chamber 33 and permits secure positioning at various angular orientations by screw clamping or otherwise locking onto wheel 37. Shaft 39 is supported by a suitable bearing arrangement (not shown) mounted on stand 40.

FIG. 1 illustrates chamber 33 rotated about 45 degrees from horizontal with the corner including the liquid inlet pointed downwardly. This orientation is used to begin filling of the slab-gel holders. More details of the slab-gel filling chamber 33 are illustrated in FIG. 2 in which the chamber is rotated to an upright position with the chamber bottom horizontal. The orientation illustrated in FIG. 2 is that which would be obtained after the slab-gel holders are filled.

The slab-gel filling and casting chamber 33, particularly as illustrated in FIG. 2, includes side walls 43, a bottom wall 45 and a removable front end wall 47 such as with threaded knurled nuts and bolts 49. The top surface may be left open for monitoring and adjusting the position of the slab-gel holders 35. To facilitate observation of the system, the chamber walls are preferably of transparent or of translucent material, i.e. of generally transparent material. Chamber 33 is of generally prismatic shape and is preferably a rectilinear prism as illustrated. Other prismatic shapes with polygonal end walls may also be suitable, provided the bottom and side wall angles extend along a sufficient proportion of the chamber volume to permit gentle filling of a solution having a density gradient as will be described below.

In order to distribute the coagulable solution into each of the plurality of slab-gel holders, various distribution means can be employed. FIG. 2 illustrates a funnel assembly 51 which extends lengthwise between the end walls along the bottom of side wall 43 at the corner between the side and bottom walls. The flow of solution from line 31 is thereby spread and distributed to each of the slab-gel holders by flow into the depression or well 53 provided lengthwise along the margin of bottom wall 45.

As an alternate manner of distributing solution into each of the individual slab-gel holders, a plurality of tubes can be employed between the mixing chamber 23 and the gel casting chamber 33 with one tube communicating with each of the slab-gel holders. A peristaltic pump can be employed to accurately meter the flow through each of the plurality of tubes and provide a consistent flow of solution into each of the slab-gel holders.

In order to obtain the proper rotational alignment of the prismatic casting chamber 33, a level 42 or other attitude indicating device is illustrated installed on the back end wall of the chamber. The level can be employed to position the chamber in a level upright mode with the bottom surface parallel to horizontal as the coagulable solution transforms to the gel.

To facilitate positioning and maintaining the slab-gel holders within the prismatic chamber, the front end wall 47 is removable. The dry chamber can thus be loaded from the front end with the slab-gel holders. The complete stack or deck of holders is somewhat smaller than the width between the side walls and the length between the end walls of the prismatic chamber. Spacers or shims 54 and 55 are positioned along one side and at the back end of the holder deck to maintain position as the filling and casting operation proceeds. Inflatable plastic bags have been found to serve particularly well as the spacers 54, 55.

One particularly well suited envelope 11 for containing the solutions has been found to be a plastic bag of a material that can be thermally fused together along a curved line to form septum 13. A preferred material for this purpose is polyvinyl chloride of about one-half millimeter thickness.

The septum 13 is a curved seal of bonded, fused material between compartments 15 and 17 from the top to the bottom of the envelope 11. The shape of the curve of septum 13 can be varied to correspond to the desired density gradient for the solution. A thermal bond of this type forming a septum 13 can be achieved merely by passing an electrically heated stylus or other similar device over the outer surface of the envelope to seal the two envelope sides together along the stylus path.

Septum 13 can also be formed within envelope 11 merely by clamping the sides together along the desired curve. Two rigid bars, one on either side of envelope 11, shaped to define the septum can be mechanically fastened together at their ends by bolts or other suitable fasteners.

In one manner of employing the described system for filling slab-gel holders, two acrylimide solutions of different density are contained separately, one in each of the two compartments 15 and 17 of envelope 11. In order to begin filling the holders with low-density liquid and to continuously increase the liquid density as filling proceeds, the solution of greater density is placed in compartment 17 and that of lesser density in compartment 15.

The gradient flow is begun by permitting the two solutions to flow by gravity into the mixer 23 and subsequently to the prismatic casting chamber 33. It will be clear by examining the slant of septum 13 that the initial flow will predominate in lower density solution from compartment 15 and that the later and final flow will predominate from the higher density compartment 17. The continuous flow from these two compartments passing through mixer 23 provides a solution flow with a density gradient for filling into the prismatic casting chamber 33.

During the initial filling of chamber 33, it is rotatively positioned with the corner between bottom wall 45 and side wall 43 at the inlet pointed downwardly such that both the side and bottom walls are oblique to the horizontal as illustrated in FIG. 1. This permits the diverging angle of the side and bottom walls to provide a funneling effect and gently fill the slab-gel holders with minimal mixing of gradient portions of different density. By introducing the lower density gradient first, natural convection within the holders before polymerization is minimized. As chamber 33 and the slab-gel holders are filled, the chamber 33 is gradually and carefully rotated from its oblique position for initial filling to an upright position with the bottom wall horizontal when the filling is completed.

It has been found that this procedure of using the diverging walls of the casting chamber as a funnel permits sufficiently rapid filling of the slab-gel holders. Gel solidification does not occur appreciably prior to complete filling but yet the filling is conducted at a slow and gentle rate to minimize mixing of solution portions of different density. The resulting gel produced in the slab-gel holders is one of a gradually increasing density from top to bottom (or side to side) for use in a subsequent electrophoresis separation of proteins and protein subunits. The following example is presented merely to illustrate the use of the system described herein.

EXAMPLE

An envelope having two compartments separated by a top-to-bottom fused septum is filled with an aqueous solution of acrylamide. The first compartment includes about 25% by weight acrylamide, 0.1% SDS, 0.375 M tris (hydroxymethyl) aminomethane-HCl and a suitable polymerization catalyst. The second compartment includes about 5% by weight acrylamide and the same proportions of the other ingredients. The two solutions are allowed to flow together into the mixing vessel to provide a gradient flow which passes on to the inlet funnel of the casting chamber. The casting chamber is rotated about 45° to the horizontal with the corner including the gradient flow inlet pointed downwardly. As the casting chamber and the slab-gel holders are filled, the chamber is gently rotated to the upright position with the bottom positioned horizontally. After the gradient within the slab-gel holder transforms into a gel, the holder is removed from chamber 33 and the sample material is loaded onto an exposed edge of the gel. The electrophoresis separation described in U.S. Pat. application Ser. No. 810,443 cited above is then performed.

It will be clear that the above merely illustrates the use of a slab-gel filling system and that various changes may be made in the procedures, starting materials and agents by one skilled in the art within the scope of the claims.

The embodiments of the invention in which an exclusive property or privilege is claimed are defined as follows:

1. A system for preparing a plurality of slab gels having a density gradient between two opposite edges comrising:
   a prismatic chamber having a bottom wall, end walls and at least two side walls, for containing a plurality of slab-gel holders in an array with major surfaces of the individual holders generally parallel to the end walls of the prismatic chamber, each of the holders comprising a pair of spaced apart plates defining an intermediate volume for containing a slab gel, the prismatic chamber being rotatably supported on an axis passing transversely through its end walls, and including an inlet for coagulable solution flow at a lower longitudinal corner formed at the intersection of the bottom and a side wall;
   means for preparing and feeding a coagulable solution flow having an increasing density gradient into said inlet; and
   means for rotatably positioning said prismatic chamber with the bottom and side surfaces diverging upwardly from said lower longitudinal corner having said inlet to begin filling and means for rotating said chamber during filling such that the bottom wall is advanced to a horizontal position when filling is completed.

2. The system of claim 1 wherein said preparing and filling means include a flexible plastic envelope of thermally fusible material having first and second compartments separated by a curved septum comprising a thermally fused bond of the two opposing envelope sides along a curved line passing from top to bottom of the envelope, each of said compartments having an upper inlet and a lower outlet.

3. The system of claim 2 wherein said preparing and feeding means include a liquid mixing device connected between the outlets of both the first and second compartments for blending together a solution flow from each compartment to form a composite flow with an increasing density gradient.

4. The system of claim 1 wherein noncoagulable liquid feed means are provided to displace said solution with a colored noncoagulable liquid from the preparing and feeding means after filling said sol-gel holders.

5. The system of claim 1 wherein a diverging flow channel is provided in communication with said inlet of said prismatic chamber including an extended channel portion generally coextensive with said lower longitudinal corner.

6. The system of claim 1 wherein at least one of the end walls of said prismatic chamber is removable for loading and removing slab-gel holders.

7. The system of claim 1 wherein said prismatic chamber walls are of a generally transparent material.

* * * * *